US010786457B2

(12) United States Patent
Paborji et al.

(10) Patent No.: US 10,786,457 B2
(45) Date of Patent: *Sep. 29, 2020

(54) PHARMACEUTICAL FORMULATIONS

(71) Applicant: THERAVIDA, INC., San Mateo, CA (US)

(72) Inventors: Mehdi Paborji, San Mateo, CA (US); Robert V. Tuohy, III, Norristown, PA (US); Peter R. P. Freed, Norristown, PA (US); Roger S. Flugel, Menlo Park, CA (US)

(73) Assignee: THERAVIDA, INC., Chapel Hill, NC (US)

( * ) Notice: Subject to any disclaimer, the term of this patent is extended or adjusted under 35 U.S.C. 154(b) by 173 days.

This patent is subject to a terminal disclaimer.

(21) Appl. No.: 15/949,911

(22) Filed: Apr. 10, 2018

(65) Prior Publication Data
US 2018/0243218 A1    Aug. 30, 2018

Related U.S. Application Data

(63) Continuation of application No. 15/203,699, filed on Jul. 6, 2016, now Pat. No. 9,968,556, which is a continuation of application No. 13/078,881, filed on Apr. 1, 2011, now Pat. No. 9,415,013.

(60) Provisional application No. 61/320,202, filed on Apr. 1, 2010.

(51) Int. Cl.
| | |
|---|---|
| *A61K 9/50* | (2006.01) |
| *A61K 31/222* | (2006.01) |
| *A61K 31/4178* | (2006.01) |
| *A61K 9/16* | (2006.01) |

(52) U.S. Cl.
CPC .......... *A61K 9/1652* (2013.01); *A61K 9/1617* (2013.01); *A61K 9/1676* (2013.01); *A61K 9/5078* (2013.01); *A61K 9/5084* (2013.01); *A61K 31/222* (2013.01); *A61K 31/4178* (2013.01); *A61K 9/5047* (2013.01)

(58) Field of Classification Search
CPC .. A61K 9/5042; A61K 9/5047; A61K 9/5078; A61K 9/5084; A61K 31/222; A61K 31/4178
See application file for complete search history.

(56) References Cited

U.S. PATENT DOCUMENTS

| | | | |
|---|---|---|---|
| 4,209,505 A | 6/1980 | Mikhail | |
| 4,302,440 A | 11/1981 | John et al. | |
| 4,927,640 A | 5/1990 | Dahlinder et al. | |
| 5,674,895 A | 10/1997 | Guittard et al. | |
| 5,840,754 A | 11/1998 | Guittard et al. | |
| 6,033,685 A | 3/2000 | Qiu et al. | |
| 6,149,943 A | 11/2000 | McTeigue et al. | |
| 6,419,954 B1 | 7/2002 | Chu et al. | |
| 6,482,837 B1 | 11/2002 | Wood | |
| 6,627,635 B2 | 9/2003 | Palermo et al. | |
| 6,660,382 B2 | 12/2003 | Nouri et al. | |
| 6,692,769 B1 | 2/2004 | Ishibashi et al. | |
| 6,716,449 B2 | 4/2004 | Oshlack et al. | |
| 6,787,156 B1 | 9/2004 | Bar-Shalom | |
| 7,026,329 B2 | 4/2006 | Crain et al. | |
| 7,419,686 B2 | 9/2008 | Kaiko et al. | |
| 7,666,894 B2 | 2/2010 | Paborji | |
| 7,678,821 B2 | 3/2010 | Paborji | |
| 7,781,472 B2 | 8/2010 | Paborji | |
| 7,897,179 B2 | 3/2011 | Mulye | |
| 8,007,825 B2 | 8/2011 | Wynn et al. | |
| 8,110,226 B2 | 2/2012 | Li | |
| 8,470,864 B2 | 6/2013 | Paborji | |
| 8,652,523 B2 | 2/2014 | Guimberteau et al. | |
| 8,821,935 B2 | 9/2014 | Guimberteau et al. | |
| 8,906,419 B2 | 12/2014 | Mulye | |
| 8,940,763 B2 | 1/2015 | Paborji et al. | |
| 9,132,124 B2 | 9/2015 | Paborji et al. | |
| 9,415,013 B2 | 8/2016 | Paborji et al. | |
| 9,744,157 B2 | 8/2017 | Paborji et al. | |
| 9,968,556 B2 | 5/2018 | Paborji et al. | |
| 10,328,057 B2 | 6/2019 | McGraw, III | |

(Continued)

FOREIGN PATENT DOCUMENTS

| | | |
|---|---|---|
| CN | 101287462 A | 10/2008 |
| EP | 1629834 A1 | 3/2006 |

(Continued)

OTHER PUBLICATIONS

Extended European Search Report and Written Opinion issued in EP 18212881.9 dated Mar. 26, 2019.
First Examination Report for Indian Patent Application No. 2078/MUMNP/2013 dated Nov. 11, 2018.
Prescribing information for VESICARE(TM), Jan. 2012.
Product and Technology website [on-line]. Theravida, Inc. Mar. 9, 2015 (Mar. 9, 2015) [web archive retrieved on Mar. 10, 2016]. Retrieved from the Internet URL:—http://web.archive.org/web/20 150309011535/htlp://theravida.com/product.html> andURL:http://web .archive.org/web/20 150309011557 /http:/ / theravida .com/ technology .html>.
Cheshire et al.; (2008) "Drug-induced hyperhidrosis and hypohidrosis: incidence, prevention and management"; Drug Safety 31 (2) :pp. 109-126.

(Continued)

*Primary Examiner* — Lakshmi S Channavajjala
(74) *Attorney, Agent, or Firm* — Troutman Pepper Hamilton Sanders LLP

(57) ABSTRACT

Disclosed herein are pharmaceutical compositions comprising a plurality of first beads each comprising: a core; a first layer comprising pilocarpine or a pharmaceutically acceptable salt thereof; and a second layer comprising a first polymer. Also disclosed are pharmaceutical compositions comprising a plurality of second beads each comprising: a core; and a first layer comprising tolterodine or a pharmaceutically acceptable salt thereof. Further disclosed are pharmaceutical formulations comprising: a) a plurality of the first beads; b) a plurality of the second beads; or c) a plurality of the first beads and a plurality of the second beads.

30 Claims, No Drawings

(56) References Cited

U.S. PATENT DOCUMENTS

| | | | |
|---|---|---|---|
| 10,610,519 B2 | 4/2020 | McGraw, III | |
| 2004/0185111 A1 | 9/2004 | Rubino et al. | |
| 2005/0287211 A1 | 12/2005 | Yoshida et al. | |
| 2007/0053995 A1 | 3/2007 | Paborji | |
| 2007/0077300 A1 | 4/2007 | Wynn et al. | |
| 2007/0224269 A1 | 9/2007 | Rubino et al. | |
| 2008/0207737 A1 | 8/2008 | Zinger et al. | |
| 2008/0254115 A1 | 10/2008 | Rubino | |
| 2008/0299393 A1 | 12/2008 | Wu et al. | |
| 2009/0017111 A1 | 1/2009 | Van den Heuvel et al. | |
| 2009/0192228 A1* | 7/2009 | Wang | A61K 9/5078 514/648 |
| 2009/0247628 A1 | 10/2009 | Gant et al. | |
| 2009/0275629 A1 | 11/2009 | Paborji | |
| 2009/0318522 A1 | 12/2009 | Paborji | |
| 2010/0137392 A1 | 6/2010 | Paborji | |
| 2010/0152263 A1 | 6/2010 | Paborji | |
| 2011/0244051 A1 | 10/2011 | Paborji et al. | |
| 2011/0245294 A1 | 10/2011 | Paborji et al. | |
| 2012/0201894 A1 | 8/2012 | Paborji et al. | |
| 2012/0289543 A1 | 11/2012 | Paborji et al. | |
| 2012/0289544 A1 | 11/2012 | Paborji et al. | |
| 2013/0289087 A1 | 10/2013 | Paborji | |
| 2014/0037713 A1 | 2/2014 | Wotton et al. | |
| 2014/0105976 A1 | 4/2014 | Paborji et al. | |
| 2020/0188360 A1 | 6/2020 | McGraw, III | |

FOREIGN PATENT DOCUMENTS

| | | |
|---|---|---|
| WO | 9405263 A1 | 3/1994 |
| WO | 9709980 A1 | 3/1997 |
| WO | 98042318 A1 | 10/1998 |
| WO | 200119901 A2 | 3/2001 |
| WO | 0134139 A1 | 5/2001 |
| WO | 2001054728 A1 | 8/2001 |
| WO | 2003013538 A1 | 2/2003 |
| WO | 2003082207 A2 | 10/2003 |
| WO | 2004105735 A1 | 12/2004 |
| WO | 2005046684 A1 | 5/2005 |
| WO | 2005123042 A1 | 12/2005 |
| WO | 2006026556 A2 | 3/2006 |
| WO | 2006132196 A1 | 12/2006 |
| WO | 2007027675 A1 | 3/2007 |
| WO | 2007029087 A2 | 3/2007 |
| WO | 2007041367 A2 | 4/2007 |
| WO | 2009019599 A2 | 2/2009 |
| WO | 2009022354 A2 | 2/2009 |
| WO | 2009045796 A1 | 4/2009 |
| WO | 2009057138 A2 | 5/2009 |
| WO | 2011123815 A1 | 10/2011 |
| WO | 2011123836 A2 | 10/2011 |
| WO | 2012154770 A1 | 11/2012 |

OTHER PUBLICATIONS

Oxybutynin Chloride. Drug Facts & Comparisons, Urinary Tract Products, Dec. 1984, p. 730, Wolters Kluwer Health.

Mihnhout et al. "Oxybutynin: Dry Days for Patients with Hyperhydrosis." Netherlands: The Journal of Medicine. vol. 64, Van Zuiden Communications, Oct. 2006, pp. 326-329.

Wall et al. (2002) "Pharmacotherapy of Xerostomia in Primary Sjogren's Syndrome"; Pharmacotherapy, 22(5); pp. 621-629.

Watanabe, Kiyoshi, et al. (1986) "Oxybutynin hydrochloride: Effects of Oxybutynin hydrochloride on the Motilities of the Digestive Tracts and Urinary Bladder in Anesthetized Dogs"; Applied Pharmacology, vol. 31, No. 5; pp. 995-1106.

Yakushiji, T. et al., "Effects of Benzodiazepines and Non-Benzodiazepine Compounds on the GABA-induced Response in Frog Isolated Sensory Neurones", Br. J. Pharmacol. (1989), 98, 735-740.

Yoshida Akira et al. (2010) "The forefront for novel therapeutic agents based on the pathophysiology of lower urinary tract dysfunction: bladder selectivity based on in vivo drug-receptor binding characteristics of antimuscarinic agents fortreatment of overactive bladder"; Journal of Pharmacological Sciences, vol. 112. No. 2; pp. 142-150.

Zinner, Norman et al., "Trospium Chloride Improves Overative Bladder Symptoms: A Multicenter Phase III Trial," Journal of Urology, (2004) 171:2311-2315.

ANZCTR (A Phase 2a Study Evaluating the Safety and Efficacy of THVD-102, a combination of Oxybutynin and Pilocarpine, in Subjects with Primary Focal Hyperhidrosis, Australian New Zealand Clinical trial registry, Mar. 2015, p. 1-6) (Year: 2015).

Humbert et al. (Use of oral oxybutynin at 7.5 mg per day in primary hyperhidrosis, Rev. Med. Liege, 2012, col. 67, pp. 520-526 and English Abstract) (Year: 2012).

Iwabuchi et al. (Exploratory study on reduction of the incidence of hyperhidrosis by oral pilocarpine, J. Oral and Maxillofacial Surgery Medicine and Pathology, vol. 26, 2014, pp. 179-182) (Year: 2014).

"Pilocarpine". Drug Facts and Comparisons. 1996 Edition. pp. 2672-2675.

Aframian, D.J. et al., "Pilocarpine Treatment in a Mixed Cohort of Xerostomic Patients," Oral Diseases, (2007) 13:88-92.

Anzctr Australian New Zealand Clinical Trials Registry, Clinical Trial Description; Jul. 21, 2015; "The Safety and Efficacy of THVD-102, a combination ofOxybutynin and Pilocarpine, in Subjects with Primary Focal Hyperhidrosis"; (website) 9 pages.

Aromdee, Chantana et al., "A Pilot Study of the Disposition of Pilocarpine in Plasma, Saliva and Urine After a Single Oral Dose," European Journal of Pharmaceutical Sciences, (1999) 8:81-83.

Boz JD (2015) "Systemic Treatment of Hyperhidrosis"; Actas Dermosifiliogr. 106(4); pp. 271-277.

Chancellor, Michael B. et al., "A Comparison of the Effects on Saliva Output of Oxybutynin Chloride and Tolterodine Tartrate," Clinical Therapeutics, (2001) 23:5:753-760.

Chapple Christopher R., "Muscarinic Receptor Antagonists in the Treatment of Overactive Bladder," Urology, 55 (Supplement 5A), May 2000, 33-46.

Chapple, Christopher et al., "The Effects of Antimuscarinic Treatments in Overactive Bladder: A Systematic Review and Meta-Analysis," European Urology, (2005) 48:5-26.

Clemett, et al; (2001) "Tolterodine: a review of its use in the treatment of overactive bladder"; Drugs & Aging 18(4):277-304.

Detrol (R) Package Insert; Pfizer, Inc. Mar. 2008, 14 pgs.

Diokno, Ananias et al., "Prospective, Randomized, Double-Blind Study of the Efficacy and Tolerability of the Extended-Release Formulations of Oxybutynin and Tolterodine for Overactive Bladder: Results of the OPERA Trial," Mayo Clin Proc., (2003)78:687-695.

Eisai Inc. "Salagen: FDA Package Insert," Dec. 2009, 13 pages.

Extended European Search Report and Written Opinion issued in EP 11763548 dated Sep. 17, 2014.

Facts & Comparisons (1984), p. 730.

Foote, Jenelle et al., "Treatment of Overactive Bladder in the Older Patient: Pooled Analysis of Three Phase II Studies of Darifenacin, an M3 Selective Receptor Antagonist," European Urology, (2005) 48:471-477.

Gautam et al., "Cholinergic Stimulation of Salivary Secretion Studied with M.sub.1 and M.sub.3 Muscarinic Receptor Single- and Double-Knockout Mice"; Molecular Pharmacology, 66(2); 260-269 (Aug. 2004).

Harris, N.O. et al., (1960) "Infrared Spectral Characteristics of Pilocarpine-stimulated Saliva of Normally Caries-resistant Animals Compared with Caries-resistant and -susceptible Humans"; J. Dent. Res. 39:810-811.

Hornberger, J. et al. "Recognition, diagnosis, and treatment of primary focal hyperhidrosis"; J. Am. Acad. Dermatol. vol. 51, (Aug. 2004) pp. 274-286.

International Preliminary Report on Patentability dated Apr. 16, 2007 in PCT/US2006/033671.

Jacobs, CD, et al. (1996) "A multicenter maintenance study of oral pilocarpine tablets for radiation-induced kerostomia"; Oncology 10(3 Suppl); pp. 16-20.

(56) References Cited

OTHER PUBLICATIONS

Kim, W.O. et al. (2010) "Treatment of generalized hyperhidrosis with oxybutynin in post-menopausal patients"; Acta Derm Venereal. vol. 90; pp. 291-293.
Loscher, W. and Honack, D., "Withdrawal Precipitation by Benzodiazepine Receptor Antagonists in Dogs Chronically Treated with Diazepam or the Novel Anxiolytic and Anticonvulsant Beta-carboline Abecamil," Naunyn Schmiedebergs Arch. Pharmacol. (1992), 345, 452-460.
MacDiarmid, Scott A. et al., "Efficacy and Safety of Extended Release Oxybutynin for the Treatment of Urge Incontinence: An Analysis of Data From 3 Flexible Dosing Studies," The Journal of Urology, (2005) 174:1301-1305.
Masters, Kim J., (2005) "Pilocarpine Treatement of Xerostmia Induced by Psychoactive Medications" American Journal of Psychiatry 162(5):1023.
Nagao, Mitsuhiro, et al. (1999) "Effects of propiverine hydrochloride (propiverine) on the muscarinic receptor binding affinity in guinea pig tissues and on salivation in conscious dogs"; Folia Pharmacologica Japonica, vol. 113, No. 3; pp. 157-166.
Oki, Tomomi et al., "Comparitive Evaluation of Exocrine Muscarinic Receptor Binding Characteristics and Inhibition of Salivation of Solifenacin in Mice," Biol. Pharm. Bull, (2006) 29(7):1397-1400.
Oki, Tomomi et al., "Demonstration of Bladder Selective Muscarinic Receptor Binding by Intravesical Oxybutynin to Treat Overactive Bladder," The Journal of Urology vol. 172: (2004): pp. 2059-2064.
Oki, Tomomi et al., "Muscarinic Receptor Binding, Plasma Concentration and Inhibition of Salivation After Oral Administration of a Novel Antimuscarinic Agent, Solifenacin Succinate in Mice," British Journal of Pharmacology, (2005) 145:219-227.
Olsson, et al. (2001) "Multiple dose pharmacokinetics of a new once daily extended release tolterodine formulation versus immediate release tolterodine"; Clin Pharmacokinet. 40(3):227-235.
Paborji, M. et al: "Phase I Evaluation of THVD-201. A Fixed-Dose Combination of Tolterodine and Pilocarpine, to Eliminate the Dry Mouth Side Effect of Anti-Muscarinic Therapy for Overactive Bladder" European Urology Supplements, vol. 10. No. 2; Mar. 22, 2011; p. 277. XP008152710.
Pattee, et al. (1992) "Drug Treatment of the Irritable Bowel Syndrome"; Drugs, vol. 44, No. 2; pp. 200-206.
Physicians Desk Reference (PDR) (2002), pp. 229-2230.
Prescribing information for DETROL.TM., 2009, 14 pages, Phamacia& Upjohn Co, Mar. 2008.
Prescribing information for EMBEDA.TM., 2009, product information. 12 pages.
Rappaport, Bob A., NDA Approval letter for EMBEDA.TM., Aug. 13, 2009.
Saja Pharmaceuticals Co: "Vesicare 10 mg and 5 mg" Sep. 26, 2007 (Sep. 26, 2007). 1 page. Retrieved from the Internet: URL:http://www.sajaonline.net/pdf/Vesicare%20leaflet.pdf.
Salagen.RTM. (pilocarpine HCl) product insert (.COPYRGT. 2003 MGI Pharma, 25 Inc.)
Salah, R.S. et al., "Pilocarpine for Anticholinergic Adverse Effects Asscoaited with Desipramine Treatement"; American Journal of Psychiatry, 153(4): (1996): pp. 579.
Search and Exam Report issued by the Austrian Patent Office in Singapore Patent Application No. 201003060-9 dated Jul. 27, 2012.
Search Report and Written Opinion dated Jan. 3, 2012, issued in SG 201003060-9.
Serra, Denise B. et al., (2005) "QT and QTc Interval with Standard and Supratherapeutic Doses of Darifenacin, a Muscarinic M3 Selective Receptor Antagonist for the Treatment of Overactive Bladder"; Journal Clinical Pharmacology, 45:1038-1047.
Siami, Paul et al., "A Multicenter, Prospective, Open-Label Study of Tolterodine Extended-Release 4 mg for Overactive Bladder: The Speed of Onset of Therapeutic Assessment Trial (STAT)," Clinical Therapeutics, (2002) 24:616-628.
Smulders, Ronald A. et al., "Pharmacokinetics and Safety of Solinfenacin Succinate in Healthy Young Men," Journal of Clinical Pharmacology, (2004) 44:1023-1033.
St. Peter et al., "Pharmacokinetics of Pilocarpine in Subjects with Varying Degrees of Renal Function", J Clin Pharmacol, 40: 1470-1475, (2000).
Stedman's Medical Dictionary (published by Houghton Mifflin Company) (1995), p. 642.
Steers, William et al. (2005) "An Investigation of Dose Titration with Darifenacin, an Mx-Selective Receptor Antagonist"; BJU International 95:580-586.
Tiwari, Atul and Krishna S. Naruganahalli, "Current and Emerging Investigational Medical Therapies for the Treatment of Overactive Bladder," Expert Opin. Investig. Drugs, (2006) 15(9):1017-1037.
U.S. Department of Health and Human Services, Food and Drug Administration, Center for Drug Evaluation and Research (COER), "Guidance for Industry: Waiver of in Vivo Bioavailability and Bioequivalence Studies for Immediate-Release Solid Oral DosageForms Based on a Biopharmaceutics Classification System," Section II(C); Aug. 2000.
Versi, Eboo et al., "Dry Mouth with Conventional and Controlled-Releases Oxybutynin in Urinary Incontinence," Obstetrics & Gynecology, (2000) 95:718-721.
Waldeck, Kristian et al., "Comparison of Oxybutynin and its Active Metabolite, N-Desethyl-Oxybutynin, in the Human Detrusor and Parotid Gland," The Journal of Urology, (1997) 157:1093-1097.
Pariser et al., "Randomized, Placebo- and Active-Controlled Crossover Study of the Safety and Efficacy of THVD-102, a Fixed-dose Combination of Oxybutynin and Pilocarpine, in Subjects with Primary Focal Hyperhidrosis," J. Drugs Dermatol., Feb. 2017, vol. 16, Issue 2, pp. 127-132.

\* cited by examiner

PHARMACEUTICAL FORMULATIONS

RELATED APPLICATIONS

This application is a continuation of U.S. patent application Ser. No. 15/203,699 filed Jul. 6, 2016, which is a continuation of U.S. patent application Ser. No. 13/078,881 filed Apr. 1, 2011, now U.S. Pat. No. 9,415,013, which claims priority to U.S. Provisional Application No. 61/320,202, filed Apr. 1, 2010, by Mehdi Paborji, and entitled "PHARMACEUTICAL FORMULATIONS FOR THE TREATMENT OF OVERACTIVE BLADDER." Each of which are incorporated herein by reference in their entireties.

FIELD OF THE INVENTION

The present invention is in the field of pharmaceutical formulations, and in particular formulations comprising pilocarpine or cevimeline, formulations comprising a muscarinic antagonist, and formulations comprising a combination of pilocarpine or cevimeline and a muscarinic antagonist.

BACKGROUND OF THE DISCLOSURE

Muscarinic receptor antagonists, such as tolterodine, are known for the treatment of overactive bladder. However, an adverse side effect of these treatments is severe dry mouth. This side effect causes significant patient discomfort and reduces compliance greatly. Previous work has shown that the combination of tolterodine or oxybutynin with pilocarpine, a muscarinic receptor agonist that increases saliva formation, can significantly reduce the incidents of dry mouth while not affecting the efficacy of the muscarinic receptor antagonist. See, for example, U.S. Pat. Nos. 7,666,894, 7,678,821, and 7,781,472, and U.S. Application Publication Nos. 2009/0275629 and 2010/0152263, all of which are incorporated herein by reference in their entirety.

As discussed in the aforementioned publications, one cannot simply take a muscarinic antagonist and pilocarpine or cevimeline and expect to obtain the desired clinical efficacy. The timing of the administration of the muscarinic agonist vis-a-vis the administration of the muscarinic antagonist has to be adjusted properly so that the maximum increase in saliva formation due to the administration of the muscarinic agonist is reached at the same time as the maximum dry mouth experienced due to the administration of the muscarinic antagonist. Taking two tablets at two different times, where the time difference between the two administrations has to be exact, is inconvenient, cumbersome, and reduces patient compliance. Therefore, a single pharmaceutical formulation is needed where the desired time delay and release profile are incorporated.

SUMMARY OF THE INVENTION

Disclosed herein are pharmaceutical compositions comprising a plurality of first beads each comprising: a core; a first layer comprising pilocarpine, cevimeline, or a pharmaceutically acceptable salt thereof; and a second layer comprising a first polymer. Also disclosed are pharmaceutical compositions comprising a plurality of second beads each comprising: a core; and a first layer comprising a muscarinic antagonist or a pharmaceutically acceptable salt thereof. Further disclosed are pharmaceutical formulations comprising: a) a plurality of the first beads; b) a plurality of the second beads; or c) a plurality of the first beads and a plurality of the second beads.

DETAILED DESCRIPTION OF THE EMBODIMENTS

Aspects of the present disclosure include pharmaceutical formulations comprising a muscarinic antagonist in an immediate release formulation. Once ingested by a subject, the muscarinic antagonist in these formulations begins to release into the gut to be systemically absorbed into the blood stream. Other aspects of the present disclosure include pharmaceutical formulations comprising pilocarpine or cevimeline, both of which are muscarinic agonists. The muscarinic agonist of the pharmaceutical formulations is present in a delayed immediate release formulation. Once ingested, the muscarinic agonist is not released for some time. But once the muscarinic agonist begins to be released, it is released immediately.

In some embodiments, the muscarinic antagonist of the formulations disclosed herein is a compound that is used for the treatment of overactive bladder. In certain embodiments, the muscarinic antagonist is selected from the group consisting of tolterodine, 5-hydroxymethyl tolterodine, fesoterodine, oxybutynin, solifenacin, darifenacin, trospium, imidafenacin, propiverine, and dicyclomine.

In the context of the present disclosure, "immediate release" or "released immediately" means that at least about 70% of the ingested active pharmaceutical ingredient in the dosage form is released from the pharmaceutical formulation within about 30-60 minutes of the ingestion of the dosage form. By "not released" or "delayed released" it is meant that less than 20% of the ingested active pharmaceutical ingredient in the dosage form is released from the pharmaceutical formulation by the time the delay is concluded and the release becomes immediate.

Throughout the present disclosure the term "about" a certain value means that a range of value±10%, and preferably a range of value±5%, is contemplated. Thus, for example, having about 70% of the active pharmaceutical ingredient (API) includes API being present between 63% and 87%, and preferably between 66.5% and 73.5%; or by way of another example, "about 45 minutes" means that the contemplated value is between 40.5 minutes and 49.5 minutes, and preferably between 42.75 minutes and 47.25 minutes.

Disclosed herein are beads, or multiparticulate systems, comprising a muscarinic agonist, i.e., pilocarpine or cemiveline, and other beads comprising a muscarinic antagonist. Contemplated within the scope of the present disclosure are pharmaceutical compositions comprising muscarinic agonist beads only, muscarinic antagonist beads only, or compositions comprising both muscarinic agonist and muscarinic antagonist beads. The muscarinic agonist-only or muscarinic antagonist-only beads can be administered individually or in combination with beads or other pharmaceutical formulations comprising other active ingredients.

Muscarinic Agonist Beads

Thus, in one aspect, disclosed herein are pharmaceutical compositions comprising a plurality of first beads each comprising:

a core;

a first layer comprising a muscarinic agonist, i.e., pilocarpine or cemiveline, or a pharmaceutically acceptable salt thereof; and a second layer comprising a first polymer.

In some embodiments, the core comprises a polymer. In certain embodiments, the core polymer is a cellulose polymer. In some of these embodiments, the cellulose polymer is microcrystalline cellulose. In other embodiments, the core comprises a sugar. In certain embodiments, the sugar is selected from the group consisting of glucose, sucrose, lactose, mannitol, maltodextrine, xylitol, and sorbitol. In further embodiments, the core comprises silicon dioxide.

In some embodiments, the core is obtained commercially. An example of commercially available beads to be used as core for the beads disclosed herein includes, but is not limited to, sugar spheres (for example, Paular spheres), Cellets® cores, such as Cellets® 100, Cellets® 200, Cellets® 350, Cellets® 500, Cellets® 700, or Cellets® 1000 (Glatt Air Techniques Inc., Ramsey N.J.). In other embodiments, the core is prepared de novo, for example by preparing a polymer mixture, extruding the mixture, and spheronizing the extruded mixture to form spherical or semi-spherical beads. In some embodiments, the beads are swellable such that their exposure to aqueous media causes them to swell and release the active ingredient rapidly and efficiently.

In some embodiments, the core comprises between about 10% to about 50% of the total weight of the finally-formulated bead. In some embodiments, the core comprises between about 15% to about 40% of the total weight of the finally-formulated bead. In some embodiments, the core comprises between about 20% to about 30% of the total weight of the finally-formulated bead. In some embodiments, the core comprises about 20% of the total weight of the finally-formulated bead. In some embodiments, the core comprises about 25% of the total weight of the finally-formulated bead.

In some embodiments, a solution of the muscarinic agonist, a free base thereof or a pharmaceutically acceptable salt thereof, is prepared and then sprayed onto the core and then dried. The act of spraying and drying causes a layer (the first layer) of the API (i.e., pilocarpine or cevimeline) to form over the bead. In some embodiments, the solution comprises a polymer that causes the API to more efficiently adhere to the core. The amount of the API present in the dosage form can be controlled by controlling the thickness of the first layer and/or by the concentration of the solution comprising the API. The thicker the first layer, or the more concentrated the API solution, the more API is present in the dosage form. Once the first layer is exposed to aqueous media, for example gastric or intestinal juice, the pilocarpine contained therein immediately dissolves into the aqueous medium. Methods of applying the first layer uniformly onto the core are well-known in the art.

In some embodiments, the first layer comprises between about 1% to about 50% of the total weight of the bead. In some embodiments, the first layer comprises between about 2% to about 40% of the total weight of the bead. In some embodiments, the first layer comprises between about 5% to about 30% of the total weight of the bead. In some embodiments, the first layer comprises between about 7% to about 25% of the total weight of the bead. In some embodiments, the first layer comprises between about 8% to about 15% of the total weight of the bead. In some embodiments, the first layer comprises about 8% of the total weight of the bead. In some embodiments, the first layer comprises about 10% of the total weight of the bead. In some embodiments, the first layer comprises about 12% of the total weight of the bead. In some embodiments, the first layer comprises about 15% of the total weight of the bead.

In some embodiments, pilocarpine or cevimeline is present as the free base. In other embodiments, pilocarpine or cevimeline is present as a pharmaceutically acceptable salt. The term "pharmaceutically acceptable salt" refers to a formulation of a compound that does not abrogate the biological activity and properties of the compound. Pharmaceutical salts can be obtained by reacting a compound of the invention with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can be obtained by reacting a compound of the invention with inorganic acids such as tartric acid, oxolic acid, "carbonic acid" to form the bicarbonate or carbonate salt of the compound, acetic acid, formic acid, benzoic acid, and the like. Pharmaceutical salts can also be obtained by reacting a compound of the invention with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like. In some embodiments, the pilocarpine is pilocarpine HCl or pilocarpine nitrate.

Once the API (pilocarpine, cevimeline, or a salt thereof) is coated onto the bead, the bead is coated with a second layer. The second layer delays the exposure of the first layer to the aqueous media. The second layer comprises at least one polymer, the first polymer.

In some embodiments, the first polymer comprises a soluble film-forming polymer. By "soluble" it is meant that the polymer is soluble in aqueous media, which means that at least about 50% of the polymer has dissolved within one hour after exposure to the aqueous media. It is understood that some polymers disperse in aqueous solutions. This dispersion is not the same as dissolving. For a compound or polymer to be soluble, there needs to be a concentration of the compound or polymer in the solvent having solute-solvent interactions, as understood in the chemical arts.

In some embodiments, the first polymer is a sugar or a polysaccharide. In some of these embodiments, the sugar or polysaccharide is selected from the group consisting of cellulose, hydroxyethylcellulose, hydroxypropylcellulose, hydroxypropylmethylcellulose, carboxymethylcellulose, maltodextrin, sucrose, modified starch, a salt of alginic acid, soluble gums, and carageenan. In other embodiments, the first polymer is polyvinylpyrrolidone (PVP) or polyvinylpolypyrrolidone (PVPP).

In some embodiments, the soluble-forming polymer is a mixture of two or more polymers. In some embodiments, the mixture comprises hydroxypropylmethylcellulose (HPMC) and hydroxypropylcellulose (HPC).

In some embodiments, hydroxypropylmethylcellulose is present in between about 1% to about 50% of the total weight of the bead. In some embodiments, hydroxypropylmethylcellulose is present in between about 2% to about 40% of the total weight of the bead. In some embodiments, hydroxypropylmethylcellulose is present in between about 5% to about 30% of the total weight of the bead. In some embodiments, hydroxypropylmethylcellulose is present in between about 7% to about 25% of the total weight of the bead. In some embodiments, hydroxypropylmethylcellulose is present in between about 8% to about 15% of the total weight of the bead. In some embodiments, hydroxypropylmethylcellulose is present in about 8% of the total weight of the bead. In some embodiments, hydroxypropylmethylcellulose is present in about 10% of the total weight of the bead.

In some embodiments, hydroxypropylmethylcellulose is present in about 12% of the total weight of the bead. In some embodiments, hydroxypropylmethylcellulose is present in about 15% of the total weight of the bead.

In some embodiments, hydroxypropylcellulose is present in between about 1% to about 90% of the total weight of the bead. In some embodiments, hydroxypropylcellulose is present in between about 5% to about 40% of the total weight of the bead. In some embodiments, hydroxypropylcellulose is present in between about 10% to about 30% of the total weight of the bead. In some embodiments, hydroxypropylcellulose is present in between about 15% to about 25% of the total weight of the bead. In some embodiments, hydroxypropylcellulose is present in between about 20% to about 25% of the total weight of the bead. In some embodiments, hydroxypropylcellulose is present in about 21.50% of the total weight of the bead. In some embodiments, hydroxypropylcellulose is present in about 22.25% of the total weight of the bead. In some embodiments, hydroxypropylcellulose is present in about 22.75% of the total weight of the bead. In some embodiments, hydroxypropylcellulose is present in about 24.50% of the total weight of the bead.

In some embodiments, the second layer further comprises an insoluble film-forming polymer. By "insoluble" it is meant that the polymer is insoluble in aqueous media, which means that at most about 10% of the polymer has dissolved within one hour after exposure to the aqueous media. The presence of the insoluble film-forming polymer in the second layer causes greater delay in the exposure of the first layer to the aqueous media. The insoluble film-forming polymer and the soluble film-forming polymer form a matrix where upon exposure to the aqueous media the soluble polymer dissolves leaving pores in a network of insoluble polymer through which pores the API in the first layer leaches out into the aqueous media.

In some embodiments, the insoluble film-forming polymer is a polysaccharide. In some of these embodiments, the polysaccharide is selected from the group consisting of ethylcellulose, cellulose acetate phthalate, hydroxypropylmethylcellulose phthalate, and insoluble gums. In other embodiments, the insoluble film-forming polymer is selected from the group consisting of a polymethacrylate, a polyvinyl alcohol, shellac, and polyvinyl acetate phthalate.

In some embodiments, ethylcellulose is present in between about 1% to about 90% of the total weight of the bead. In some embodiments, ethylcellulose is present in between about 5% to about 40% of the total weight of the bead. In some embodiments, ethylcellulose is present in between about 10% to about 30% of the total weight of the bead. In some embodiments, ethylcellulose is present in between about 15% to about 25% of the total weight of the bead. In some embodiments, ethylcellulose is present in between about 20% to about 25% of the total weight of the bead. In some embodiments, ethylcellulose is present in about 21.50% of the total weight of the bead. In some embodiments, ethylcellulose is present in about 22.25% of the total weight of the bead. In some embodiments, ethylcellulose is present in about 22.75% of the total weight of the bead. In some embodiments, ethylcellulose is present in about 24.50% of the total weight of the bead.

In some embodiments, the second layer comprises hydroxypropylcellulose and ethylcellulose. In some embodiments, the ratio of hydroxypropylcellulose to ethylcellulose is between about 5:1 to about 1:5 by weight. In some embodiments, the ratio of hydroxypropylcellulose to ethylcellulose is between about 4:1 to about 1:4 by weight. In some embodiments, the ratio of hydroxypropylcellulose to ethylcellulose is between about 3:1 to about 1:3 by weight. In some embodiments, the ratio of hydroxypropylcellulose to ethylcellulose is between about 2:1 to about 1:2 by weight. In some embodiments, the ratio of hydroxypropylcellulose to ethylcellulose is about 1:1 by weight.

In some embodiments, the first bead further comprises a de-tackifier or a glidant. In some embodiments, the de-tackifier or glidant is an inert mineral. An inert mineral is a mineral, i.e., an inorganic compound or salt, that is pharmaceutically acceptable and does not interfere with the pharmacological action of the therapeutic compound. In some embodiments, the inert mineral is a mineral of magnesium. In other embodiments, the mineral of magnesium is magnesium silicate. In certain embodiments, the de-tackifier or glidant is selected from the group consisting of talc, a monoglyceride, a diglyceride, glyceryl monostearate, calcium stearate, and magnesium stearate.

In some embodiments, the de-tackifier or glidant is present in between about 1% to about 50% of the total weight of the bead. In some embodiments, the de-tackifier or glidant is present in between about 2% to about 40% of the total weight of the bead. In some embodiments, the de-tackifier or glidant is present in between about 3% to about 20% of the total weight of the bead. In some embodiments, the de-tackifier or glidant is present in between about 4% to about 10% of the total weight of the bead. In some embodiments, the de-tackifier or glidant is present in about 4% of the total weight of the bead. In some embodiments, the de-tackifier or glidant is present in about 4.5% of the total weight of the bead. In some embodiments, the de-tackifier or glidant is present in about 5% of the total weight of the bead. In some embodiments, the de-tackifier or glidant is present in about 5.5% of the total weight of the bead. In some embodiments, the de-tackifier or glidant is present in about 6% of the total weight of the bead. In some embodiments, the de-tackifier or glidant is present in about 6.5% of the total weight of the bead.

In some embodiments, the first polymer is, or comprises, a lipid excipient. The lipid excipient can be selected from the group consisting of glyceryl behenate, glycerol esters of fatty acids, glyceryl dibehenate, behenoyl macrogoglycerides, glyceryl distearate, glycerol distearate, glyceryl palmitostearate, lauroyl macrogoglycerides, stearoyl macrogoglycerides, abitec products, glyceryl mono-oleate, medium chain mono- & diglycerides, glyceryl monocaprylate, glyceryl tricaprylate/caprate/stearate, hydrogenated vegetable oil, hydrogenated cottonseed oil, hydrogenated soybean oil, hydrogenated soybean oil and castor wax, polyoxyethylene 8 caprylic/capric glycerides, polyoxyethylene 6 caprylic/capric glycerides, polyoxyethylene 32 lauric glycerides, polyoxyethylene 6 prop. Glycol esters, polyoxyethylene 7 coconut glycerides, polyoxyethylene 30 coconut glycerides, polyoxyethylene 80 coconut glycerides, polyoxypropylene 15 stearyl ether, polyoxyethylene 26 glyceryl ether, polyoxyethylene 35 soybean glycerides, polyoxyethylene 20 sorbitol, polyoxypropylene myristyl ether, polyoxypropylene 10 cetostearyl ether, palm kernelamide diethanolamide, triglycerol mono-oleate, sasol products, hydrogenated cocoglycerides, cetyl palmitate, trimyristin, tripalmitin, tristearin, hydrogenated palm oil, glyceryl monostearate, glyceryl stearate, cetearyl alcohol, cetyl alchohol, capric triglyceride, acetylated glycerides, glyceryl cocoate, and polyethylene glycol.

In some embodiments, the first bead further comprises a plasticizer. In some embodiments, the plasticizer is selected from the group consisting of a phthalate-based plasticizer, a trimellitate, an adipate-based plasticizer, a sebacate-based plasticizer, an organophosphate, a maleate, a sulfonamide, a glycols or polyether, an acetylated monoglyceride, and an alkyl citrate.

In some embodiments, the phthalate-based plasticizer is selected from the group consisting of bis(2-ethylhexyl) phthalate (DEHP), diisononyl phthalate (DINP), bis(n-butyl)phthalate (DnBP, DBP), butyl benzyl phthalate (BBzP), diisodecyl phthalate (DIDP), di-n-octyl phthalate (DOP or DnOP), diisooctyl phthalate (DIOP), diethyl phthalate (DEP), diisobutyl phthalate (DIBP), and di-n-hexyl phthalate. In some embodiments, the trimellitate is selected from the group consisting of trimethyl trimellitate (TMTM), tri-(2-ethylhexyl) trimellitate (TEHTM-MG), tri-(n-octyl,n-decyl) trimellitate (ATM), tri-(heptyl,nonyl) trimellitate (LTM), and n-octyl trimellitate (OTM). In some embodiments, the adipate-based plasticizer is selected from the group consisting of bis(2-ethylhexyl)adipate (DEHA), dimethyl adipate (DMAD), monomethyl adipate (MMAD), and dioctyl adipate (DOA). In some embodiments, the sebacate-based plasticiser is dibutyl sebacate (DBS). In some embodiments, the maleate is dibutyl maleate (DBM) or diisobutyl maleate (DIBM). In some embodiments, the sulfonamide is selected from the group consisting of ortho or para N-ethyl toluene sulfonamide (ETSA), N-(2-hydroxypropyl) benzene sulfonamide (HP BSA), and N-(n-butyl) benzene sulfonamide (BBSA-NBBS). In some embodiments, the organophosphate is tricresyl phosphate (TCP) or tributyl phosphate (TBP). In some embodiments, the glycol or polyether is selected from the group consisting of triethylene glycol dihexanoate (3G6, 3GH), tetraethylene glycol diheptanoate (4G7), and polyethylene glycol. In some embodiments, the alkyl citrate is selected from the group consisting of Triethyl citrate (TEC), acetyl triethyl citrate (ATEC), tributyl citrate (TBC), acetyl tributyl citrate (ATBC), trioctyl citrate (TOC), acetyl trioctyl citrate (ATOC), trihexyl citrate (THC), acetyl trihexyl citrate (ATHC), butyryl trihexyl citrate (BTHC, trihexyl o-butyryl citrate), and trimethyl citrate (TMC). In some embodiments, the plasticizer is selected from the group consisting of dibutyl sebacate, polyethylene glycol, glycerin, triacetin, diethyl phthalate, propylene glycol, triethyl citrate, mineral oil, an acetylated monoglyceride, and oleic acid.

In some embodiments, the plasticizer is present in between about 1% to about 50% of the total weight of the bead. In some embodiments, the plasticizer is present in between about 2% to about 40% of the total weight of the bead. In some embodiments, the plasticizer is present in between about 3% to about 20% of the total weight of the bead. In some embodiments, the plasticizer is present in between about 4% to about 10% of the total weight of the bead. In some embodiments, the plasticizer is present in about 4% of the total weight of the bead. In some embodiments, the plasticizer is present in about 4.5% of the total weight of the bead. In some embodiments, the plasticizer is present in about 5% of the total weight of the bead. In some embodiments, the plasticizer is present in about 5.5% of the total weight of the bead. In some embodiments, the plasticizer is present in about 6% of the total weight of the bead. In some embodiments, the plasticizer is present in about 6.5% of the total weight of the bead.

In some embodiments, the weight of the second layer is between about 50% to about 300% of the weight of the bead prior to the application of the second layer. In some embodiments, the weight of the second layer is between about 75% to about 250% of the weight of the bead prior to the application of the second layer. In some embodiments, the weight of the second layer is about 75% of the weight of the bead prior to the application of the second layer. In some embodiments, the weight of the second layer is about 100% of the weight of the bead prior to the application of the second layer. In some embodiments, the weight of the second layer is about 125% of the weight of the bead prior to the application of the second layer. In some embodiments, the weight of the second layer is about 150% of the weight of the bead prior to the application of the second layer. In some embodiments, the weight of the second layer is about 175% of the weight of the bead prior to the application of the second layer. In some embodiments, the weight of the second layer is about 200% of the weight of the bead prior to the application of the second layer. In some embodiments, the weight of the second layer is about 225% of the weight of the bead prior to the application of the second layer. In some embodiments, the weight of the second layer is about 250% of the weight of the bead prior to the application of the second layer.

Muscarinic Antagonist Beads

In another aspect, disclosed herein are pharmaceutical compositions comprising a plurality of second beads each comprising:
a core; and
a first layer comprising a muscarinic antagonist or a pharmaceutically acceptable salt thereof.

In some embodiments, the muscarinic antagonist is present as the free base. In other embodiments, the muscarinic antagonist is present as a pharmaceutically acceptable salt. Pharmaceutically acceptable salts are defined above. In some embodiments, the muscarinic antagonist is selected from the group consisting of tolterodine, 5-hydroxymethyl tolterodine, fesoterodine, oxybutynin, solifenacin, darifenacin, trospium, imidafenacin, propiverine, and dicyclomine. In some embodiments, the tolterodine is tolterodine tartrate. In other embodiments, the oxybutynin is oxybutynin chloride.

In some embodiments, the core of the plurality of the second beads is comprised of the same material as the core of the plurality of the first beads, discussed above.

In some embodiments, the core comprises between about 10% to about 90% of the total weight of the finally-formulated bead. In some embodiments, the core comprises between about 25% to about 85% of the total weight of the finally-formulated bead. In some embodiments, the core comprises between about 40% to about 80% of the total weight of the finally-formulated bead. In some embodiments, the core comprises about 80% of the total weight of the finally-formulated bead. In some embodiments, the core comprises about 75% of the total weight of the finally-formulated bead. In some embodiments, the core comprises about 85% of the total weight of the finally-formulated bead.

In some embodiments, a solution of the API (i.e., the muscarinic antagonist), or a pharmaceutically acceptable salt thereof, is prepared and then sprayed onto the core and then dried. The act of spraying and drying causes a layer (the first layer) of the API to form over the bead. In some embodiments, the solution comprises a polymer that causes the API to more efficiently adhere to the core. The amount of the API present in the dosage form can be controlled by controlling the thickness of the first layer. The thicker the first layer the more API is present in the dosage form. Once the first layer is exposed to aqueous media, for example gastric or intestinal juice, the tolterodine contained therein immediately dissolves into the aqueous medium. Methods of applying the first layer uniformly onto the core are well-known in the art.

In some embodiments, the first layer comprises between about 1% to about 50% of the total weight of the bead. In some embodiments, the first layer comprises between about 2% to about 40% of the total weight of the bead. In some embodiments, the first layer comprises between about 4% to about 25% of the total weight of the bead. In some embodiments, the first layer comprises between about 5% to about 15% of the total weight of the bead. In some embodiments, the first layer comprises between about 5.5% to about 10% of the total weight of the bead. In some embodiments, the first layer comprises about 6% of the total weight of the bead. In some embodiments, the first layer comprises about 6.5% of the total weight of the bead. In some embodiments, the first layer comprises about 7% of the total weight of the bead. In some embodiments, the first layer comprises about 8% of the total weight of the bead.

In some embodiments, the first layer comprises a soluble film-forming polymer, as defined above.

In some embodiments, hydroxypropylmethylcellulose is present in between about 1% to about 50% of the total weight of the bead. In some embodiments, hydroxypropylmethylcellulose is present in between about 2% to about 40% of the total weight of the bead. In some embodiments, hydroxypropylmethylcellulose is present in between about 5% to about 30% of the total weight of the bead. In some embodiments, hydroxypropylmethylcellulose is present in between about 7% to about 25% of the total weight of the bead. In some embodiments, hydroxypropylmethylcellulose is present in between about 8% to about 15% of the total weight of the bead. In some embodiments, hydroxypropylmethylcellulose is present in about 8% of the total weight of the bead. In some embodiments, hydroxypropylmethylcellulose is present in about 10% of the total weight of the bead. In some embodiments, hydroxypropylmethylcellulose is present in about 12% of the total weight of the bead. In some embodiments, hydroxypropylmethylcellulose is present in about 15% of the total weight of the bead.

In some embodiments, the second bead further comprises a de-tackifier or a glidant, as defined above. In some embodiments, the de-tackifier or glidant is present in between about 1% to about 50% of the total weight of the bead. In some embodiments, the de-tackifier or glidant is present in between about 2% to about 40% of the total weight of the bead. In some embodiments, the de-tackifier or glidant is present in between about 3% to about 20% of the total weight of the bead. In some embodiments, the de-tackifier or glidant is present in between about 4% to about 10% of the total weight of the bead. In some embodiments, the de-tackifier or glidant is present in about 3% of the total weight of the bead. In some embodiments, the de-tackifier or glidant is present in about 3.5% of the total weight of the bead. In some embodiments, the de-tackifier or glidant is present in about 4% of the total weight of the bead. In some embodiments, the de-tackifier or glidant is present in about 4.5% of the total weight of the bead. In some embodiments, the de-tackifier or glidant is present in about 5% of the total weight of the bead. In some embodiments, the de-tackifier or glidant is present in about 5.5% of the total weight of the bead.

In some embodiments, the first layer further comprises a lipid excipient. The lipid excipient can be selected from the group consisting of glyceryl behenate, glycerol esters of fatty acids, glyceryl dibehenate, behenoyl macrogoglycerides, glyceryl distearate, glycerol distearate, glyceryl palmitostearate, lauroyl macrogoglycerides, stearoyl macrogoglycerides, abitec products, glyceryl mono-oleate, medium chain mono- & diglycerides, glyceryl monocaprylate, glyceryl tricaprylate/caprate/stearate, hydrogenated vegetable oil, hydrogenated cottonseed oil, hydrogenated soybean oil, hydrogenated soybean oil and castor wax, polyoxyethylene 8 caprylic/capric glycerides, polyoxyethylene 6 caprylic/capric glycerides, polyoxyethylene 32 lauric glycerides, polyoxyethylene 6 prop. glycol esters, polyoxyethylene 7 coconut glycerides, polyoxyethylene 30 coconut glycerides, polyoxyethylene 80 coconut glycerides, polyoxypropylene 15 stearyl ether, polyoxyethylene 26 glyceryl ether, polyoxyethylene 35 soybean glycerides, polyoxyethylene 20 sorbitol, polyoxypropylene 3 myristyl ether, polyoxypropylene 10 cetostearyl ether, palm kernelamide diethanolamide, triglycerol mono-oleate, sasol products, hydrogenated cocoglycerides, cetyl palmitate, trimyristin, tripalmitin, tristearin, hydrogenated palm oil, glyceryl monostearate, glyceryl stearate, cetearyl alcohol, cetyl alchohol, capric triglyceride, acetylated glycerides, glyceryl cocoate, and polyethylene glycol.

In some embodiments, the second bead further comprises a plasticizer, as defined above. In some embodiments, the plasticizer is polyethylene glycol. In certain embodiments, the polyethylene glycol is PEG 400.

In some embodiments, the plasticizer is present in between about 0.1% to about 50% of the total weight of the bead. In some embodiments, the plasticizer is present in between about 0.1% to about 40% of the total weight of the bead. In some embodiments, the plasticizer is present in between about 0.1% to about 5% of the total weight of the bead. In some embodiments, the plasticizer is present in between about 0.2% to about 2% of the total weight of the bead. In some embodiments, the plasticizer is present in about 0.1% of the total weight of the bead. In some embodiments, the plasticizer is present in about 0.15% of the total weight of the bead. In some embodiments, the plasticizer is present in about 0.2% of the total weight of the bead. In some embodiments, the plasticizer is present in about 0.25% of the total weight of the bead. In some embodiments, the plasticizer is present in about 0.3% of the total weight of the bead. In some embodiments, the plasticizer is present in about 0.35% of the total weight of the bead. In some embodiments, the plasticizer is present in about 0.4% of the total weight of the bead.

In some embodiments, the second beads further comprise a second layer. In some embodiments, the second layer comprises ingredients similar to the first layer, discussed above, except that the second layer does not have any API. In some embodiments, the first layer and the second layer have identical set of ingredients, whereas in other embodiments, the first and second layers have different combination of ingredients.

Pharmaceutical Formulations

In another aspect, disclosed herein are pharmaceutical formulations comprising one of the following combinations of the above beads: a) a plurality of the first beads; b) a plurality of the second beads; or c) a plurality of the first beads and a plurality of the second beads.

The disclosed pharmaceutical formulations contain sufficient number of beads to provide a single administrable dose to a subject. In some embodiments, a single administrative dose for the muscarinic agonist is between 0.5-50 mg. In certain embodiments, a single administrable dose of pilocarpine is selected from the group consisting of 3 mg, 4 mg, 5 mg, 6 mg, 10 mg, 11 mg, and 12 mg. In other embodiments, a single administrable dose of cevimeline is selected from the group consisting of 5 mg, 10 mg, 15 mg, 20 mg, 25 mg, 30 mg, 40 mg, 50 mg, and 60 mg. In certain embodiments, a single administrable dose for the muscarinic antagonist is between 0.1-100 mg. In certain embodiments, a single administrative dose is selected from the group consisting of 0.1 mg, 0.2 mg, 0.4 mg, 0.5 mg, 1 mg, 2 mg, 3 mg, 4 mg, 5 mg, 6 mg, 7 mg, 7.5 mg, 8 mg, 10 mg, 12 mg, 15 mg, 30 mg, and 60 mg.

In some embodiments, the pharmaceutical formulations are in the form of capsules. The capsules may include push-fit capsules made of gelatin, push-fit capsules, for example those made of hydroxypropylmethylcellulose, banded push-fit capsules, as well as soft, sealed capsules made of gelatin and a plasticizer, such as glycerol or sorbitol.

In some embodiments, the pharmaceutical formulations are in the form of dose sipping straws. In some embodiments, the beads are filled into a straw and a patient then drinks liquid through the straw, and through the process of drinking, the liquid pulled through the straw brings the beads into the mouth along with the liquid.

In some embodiments, the pharmaceutical formulations are in the form of dry sachets. In some embodiments, the beads are sprinkled onto food or mixed into a drink from dry sachet, and taken orally. For the dosage to be effective, the disclosed beads are filled into a sachet pouch, along with additional excipients needed to form a readily dispersible suspension. When the pouch is opened and the contents are poured over food or into a drink, the beads and additional excipients are mixed with the food or the drink, and form a palatable dispersion that is ingested by the subject. Excipients, such as salivants and glidants, are added for the contents to be easily swallowed with a minimum of chewing so that the coatings are not broken in the mouth.

In some embodiments, the pharmaceutical formulations are in the form of ready-to-use sachets. In some embodiments, the beads are premixed with an edible, high viscosity food substance (for example, yogurt, or energy gel), and the entire contents of the package is taken orally. Excipients, such as salivants and glidants, are added for the contents to be easily swallowed with a minimum of chewing so that the coatings are not broken in the mouth.

In some embodiments, the pharmaceutical formulations are in the form of suspensions. In some embodiments, the suspensions comprise ingredients such as glycerin, microcrystalline cellulose, carboxymethyl cellulose sodium, sorbitol solution, xanthan gum, and the like, and various colorings and flavorings to make the suspension palatable for pediatric or geriatric use.

In some embodiments, the first beads disclosed above, having pilocarpine or a pharmaceutically acceptable salt thereof, and the first and second layers, are coated with a third layer comprising tolterodine, or a pharmaceutically acceptable salt thereof. The third layer is the same as, or similar to, the first layer of the second beads discussed above. In certain embodiments, the tolterodine-coated first bead is further coated with a fourth layer, which is the same as, or similar to, the second layer of the second beads discussed above.

EXAMPLES

Example 1

Materials Used in the Bead Manufacturing Process

The raw materials listed in Table 1 were used in the production of the pilocarpine and tolterodine beads.

TABLE 1

Components Used for Bead Production

| Generic Name | Trade Name | Supplier |
|---|---|---|
| Pilocarpine Hydrochloride | Pilocarpine HCl | Boehringer Ingelheim |
| Tolterodine Tartrate | Tolterodine tartrate | Medichem |
| Ethylcellulose | Ethylcellulose N10 | Hercules |
| Ethylcellulose | Ethylcellulose N7 | Hercules |
| Hydroxypropyl Methylcellulose | Pharmacoat 606 | Shin Etsu |
| Hydroxypropyl Cellulose | Klucel EF | Hercules |
| Polyethylene Glycol 400 | Carbowax 400 | Dow |
| Dibutyl Sebacate | Dibutyl Sebacate | Vertellus |
| Talc | Luzenac Talc | Minerals and Pigments |
| Dehydrated Alcohol, 200 proof | Ethanol | Spectrum |
| Microcrystalline Cellulose Beads | Cellets 700 | Glatt |
| GMS Emulsion | Plasacryl | Emerson |
| Microcrystalline Cellulose | Avicel PH 101 | FMC |
| Milled Lactose | Pharmatose 200M | DMV |
| Croscarmellose Sodium | Ac-Di-Sol | FMC |
| Crospovidone | Polyplasdone XL-10 | ISP |
| Gelatin Capsules | Conisnaps, size 2 | Capsugel |
| Sterile water for Irrigation | Water | Hospira |
| Deionized water | Deionized water | N/A |

The equipment listed in Table 2 was used for the preparation of the beads.

TABLE 2

Equipment Used for Bead Production

| Equipment | Manufacturer | Location |
|---|---|---|
| FLM-1 fluid bed | Vector Corporation | Marion, IA |
| FLM-3 fluid bed | Vector Corporation | Marion, IA |
| DG-L1 Extruder | LCI | Charlotte, NC |
| QJ-230 Spheronizer | LCI | Charlotte, NC |
| Blend Master V-blender | Patterson Kelly | East Stroudsburg, PA |
| In Cap Automatic Encapsulator | Dott. Bonapace & C. | Milan, Italy |
| ProFill 100 Manual Encapsulator | Capsugel | Greenwood, SC |
| Portable Dehumidifier | DRI-EAZ | Burlington, WA |

Example 2

Dissolution Rate Determination

This method describes the procedure for the determination of the dissolution rate of the pilocarpine HCl and tolterodine tartrate combination formulations by using a reverse-phase, gradient, high-pressure liquid chromatography (HPLC) method, using techniques well-known in the art.

Stock solutions of pilocarpine HCl and tolterodine tartrate were prepared as working standards. Beads containing pilocarpine HCl and tolterodine tartrate are separately mixed with a fixed volume of 0.1 N HCl. At fixed time points after the mixing has begun, aliquots of the dissolution mixtures are injected into HPLC followed by several aliquots of the working standards. The amounts of released (dissolved) tolterodine and pilocarpine entities of formulations were calculated using the corresponding peak areas of tolterodine and pilocarpine.

A USP 2 Paddles method with the following conditions was employed to determine dissolution of various formulations.
  Dissolution media: 0.1 N HCl
  Agitation Rate: 50 RPM
  Vessel Temp: 37° C.±0.5° C.
  Sample Volume: 1.0 mL
  Disso Volume: 500 mL Example 3

Bead Formation

Beads were produced by drug layering microcrystalline cellulose beads with aqueous, cellulosic coating systems containing pilocarpine HCl or tolterodine tartrate. The beads were formulated into single dose units. The coating formulations are displayed in Tables 3 and 4 below:

TABLE 3

Sample A: Tolterodine Tartrate Drug Layering:

| Component | mg/unit | % w/w |
|---|---|---|
| Microcrystalline Cellulose Beads | 25.0 | 79.4 |
| Tolterodine Tartrate | 2.0 | 6.3 |
| HPMC | 3.1 | 9.8 |
| Talc | 1.1 | 3.5 |
| PEG 400 | 0.3 | 1.0 |
| Total | 31.5 | 100.0 |

TABLE 4

Sample B: Pilocarpine HCl drug layering:

| Component | mg/unit | % w/w |
|---|---|---|
| Microcrystalline Cellulose Beads | 27.5 | 50.0 |
| Pilocarpine HCl | 11.0 | 20.0 |
| HPMC | 11.0 | 20.0 |
| Talc | 5.5 | 10.0 |
| Total | 55.0 | 100.0 |

Both coating solutions were applied to the Microcrystalline Cellulose (MCC) Pellets using a Vector FLM-1 fluid bed with a Wurster coating configuration. Beads were hand-filled into size 2 gelatin capsules and tested for dissolution using the procedure of Example 2. The dissolution data of the drug layered beads are shown in Tables 5 and 6:

TABLE 5

Sample A: Tolterodine Tartrate Release Data
% Dissolved at Time Point (min)

| Vessel # | 0 | 5 | 12 | 20 | 30 | 45 | 60 |
|---|---|---|---|---|---|---|---|
| V1 | 0 | 77 | 109 | 113 | 113 | 114 | 114 |
| V2 | 0 | 71 | 100 | 104 | 106 | 108 | 108 |
| V3 | 0 | 45 | 96 | 106 | 111 | 113 | 113 |
| V4 | 0 | 43 | 100 | 109 | 112 | 113 | 113 |
| V5 | 0 | 61 | 100 | 105 | 108 | 110 | 110 |
| V6 | 0 | 43 | 92 | 107 | 111 | 113 | 113 |
| Mean | 0 | 56 | 99 | 107 | 110 | 111 | 112 |
| SD | 0 | 15.1 | 5.7 | 3.2 | 2.5 | 2.4 | 2.3 |
| % RSD | 0.00% | 26.73% | 5.74% | 2.96% | 2.29% | 2.17% | 2.04% |

TABLE 6

Sample B: Pilocarpine HCl Release Data
% Dissolved at Time Point (min)

| Vessel # | 0 | 10 | 20 | 30 | 45 | 60 |
|---|---|---|---|---|---|---|
| V1 | 0 | 100 | 104 | 105 | 105 | 105 |
| V2 | 0 | 99 | 106 | 106 | 106 | 106 |
| V3 | 0 | 102 | 106 | 107 | 106 | 106 |
| V4 | 0 | 101 | 106 | 106 | 107 | 107 |
| V5 | 0 | 105 | 108 | 108 | 108 | 108 |
| V6 | 0 | 93 | 109 | 109 | 109 | 109 |
| Mean | 0 | 100 | 107 | 107 | 107 | 107 |
| SD | 0 | 4.0 | 1.8 | 1.5 | 1.5 | 1.5 |
| % RSD |  | 4.0% | 1.7% | 1.4% | 1.4% | 1.4% |

Both types of drug layered beads were top-coated. The tolterodine beads were coated with a thin, immediate release HPMC based coating system to ensure no tolterodine tartrate was lost from erosion. The topcoat for the pilocarpine HCl beads was developed in rounds 2-5 of development.

Example 4

Bead Formation

The development in this example focused on the use of several types and grades of cellulosic polymers in order to form a semi-permeable barrier that would delay release. All coatings applied were at relatively low weight gains, no higher than 50%. It was determined that the application of high weight gains produced the desired delayed release profile. The formulations and release profiles are summarized in Table 7 below:

TABLE 7

Formulations

| Reference | Film Component | % w/w |
|---|---|---|
| A | HPMC 606 | 40 |
|  | EC N10 | 40 |
|  | Talc | 20 |
| C | HPC EF | 24 |
|  | EC N7 | 56 |
|  | Talc | 20 |
| D | HPC EF | 32 |
|  | EC N7 | 48 |
|  | Talc | 20 |
| E | HPC EF | 24 |
|  | EC N10 | 56 |
|  | Talc | 20 |

TABLE 7-continued

Formulations

| Reference | Film Component | % w/w |
|---|---|---|
| F | HPC EF | 87 |
|   | Plasacryl | 13 |
| G | EC N7 | 90.9 |
|   | Dibutyl Sebacate | 9.1 |
| H | EC N10 | 90.9 |
|   | Dibutyl Sebacate | 9.1 |

The dissolution data of the beads of Samples F and G, obtained using the procedure of Example 2, are shown in Tables 8 and 9:

TABLE 8

Sample F Dissolution Data
% Dissolved at Time Point (min)

| Vessel # | 0 | 10 | 20 | 30 | 45 | 60 | 75 | 90 | 120 | Infinity |
|---|---|---|---|---|---|---|---|---|---|---|
| V1 | 0 | 9 | 48 | 71 | 84 | 89 | 96 | 99 | 101 | 101 |
| V2 | 0 | 9 | 50 | 77 | 92 | 95 | 96 | 97 | 97 | 97 |
| Mean | 0 | 9 | 49 | 74 | 88 | 92 | 96 | 98 | 99 | 99 |
| SD | 0 | 0.0 | 1.4 | 4.2 | 5.7 | 4.2 | 0.0 | 1.4 | 2.8 | 2.8 |
| % RSD |   | 0.0% | 2.9% | 5.7% | 6.4% | 4.6% | 0.0% | 1.4% | 2.9% | 2.9% |

TABLE 9

Sample G Dissolution Data
% Dissolved at Time Point (min)

| Vessel # | 0 | 10 | 20 | 30 | 45 | 60 | 75 | 90 | 120 | Infinity |
|---|---|---|---|---|---|---|---|---|---|---|
| V1 (1%)* | 0 | 53 | 73 | 84 | 92 | 96 | 99 | 100 | 102 | 102 |
| V2 (1%)* | 0 | 55 | 73 | 84 | 93 | 99 | 102 | 103 | 104 | 104 |
| Mean | 0 | 54 | 73 | 84 | 93 | 98 | 101 | 102 | 103 | 103 |
| SD | 0 | 1.4 | 0.0 | 0.0 | 0.7 | 2.1 | 2.1 | 2.1 | 1.4 | 1.4 |
| % RSD |   | 2.6% | 0.0% | 0.0% | 0.8% | 2.2% | 2.1% | 2.1% | 1.4% | 1.4% |
| V3 (4%)* | 0 | 2 | 8 | 21 | 42 | 59 | 71 | 81 | 92 | 96 |
| V4 (4%)* | 0 | 2 | 9 | 22 | 43 | 59 | 71 | 82 | 91 | 95 |
| Mean | 0 | 2 | 9 | 22 | 43 | 59 | 71 | 82 | 92 | 96 |
| SD | 0 | 0.0 | 0.7 | 0.7 | 0.7 | 0.0 | 0.0 | 0.7 | 0.7 | 0.7 |
| % RSD |   | 0.0% | 8.3% | 3.3% | 1.7% | 0.0% | 0.0% | 0.9% | 0.8% | 0.7% |
| V5 (8%)* | 0 | 1 | 4 | 7 | 14 | 22 | 32 | 41 | 57 | 65 |
| V6 (8%)* | 0 | 1 | 3 | 5 | 11 | 19 | 28 | 36 | 52 | 61 |
| Mean | 0 | 1 | 4 | 6 | 13 | 21 | 30 | 39 | 55 | 63 |
| SD | 0 | 0.0 | 0.7 | 1.4 | 2.1 | 2.1 | 2.8 | 3.5 | 3.5 | 2.8 |
| % RSD |   | 0.0% | 20.2% | 23.6% | 17.0% | 10.3% | 9.4% | 9.2% | 6.5% | 4.5% |

*The percentages refer to different film thicknesses.

Example 5
Bead Formation

In this example, swellable beads containing pilocarpine HCl were produced. First, placebo beads were produced in order to compare two common super-disintegrants. The criterion for super-disintegrant selection was volume increase as the beads were placed in 0.1 N HCl. The formulations and results are below in Table 9:

TABLE 9

Placebo bead formulations

| Experiment Reference | Bead Component | % w/w |
|---|---|---|
| I | Microcrystalline Cellulose | 45 |
|   | Lactose | 45 |
|   | Croscarmellose Sodium | 10 |

TABLE 9-continued

Placebo bead formulations

| Experiment Reference | Bead Component | % w/w |
|---|---|---|
| J | Microcrystalline Cellulose | 45 |
|   | Lactose | 45 |
|   | Crospovidone | 10 |

Two swellable pilocarpine HCl bead formulations were produced, with differing quantities of pilocarpine. These beads were then each coated with the same ethylcellulose based coating system and tested for dissolution. The formulations and results are set forth below in Table 10.

TABLE 10

Pilocarpine HCl swellable bead formulations

| Experiment Reference | Component | % w/w |
|---|---|---|
| K bead | Microcrystalline Cellulose | 40.6 |
|   | Lactose | 40.6 |
|   | Croscarmellose Sodium | 8.8 |
|   | Pilocarpine HCl | 10.0 |
| L bead | Microcrystalline Cellulose | 43.1 |
|   | Lactose | 43.1 |
|   | Crospovidone | 8.8 |
|   | Pilocarpine HCl | 5.0 |
| K and L coating formulation | Ethylcellulose N7 | 90.9 |
|   | Dibutyl Sebacate | 9.1 |

As shown in the dissolution data in Table 11, the formulations had the desired delayed release, obtained using the procedure of Example 2.

TABLE 11

Samples K and L Dissolution Data
% Dissolved at Time Point (min)

| Vessel # | 0 | 10 | 20 | 30 | 45 | 60 | Infinity |
|---|---|---|---|---|---|---|---|
| K-1 (4%) | 0 | 1 | 4 | 17 | 44 | 61 | 72 |
| K-2 (8%) | 0 | 0 | 0 | 1 | 3 | 7 | 12 |
| K-3 (12%) | 0 | 0 | 0 | 0 | 1 | 2 | 3 |
| L-1 (4%) | 0 | 1 | 4 | 12 | 29 | 42 | 53 |
| L-2 (8%) | 0 | 0 | 0 | 1 | 2 | 5 | 10 |
| L-3 (12%) | 0 | 0 | 0 | 1 | 1 | 3 | 4 |

Example 6

Bead Formation

This example focused on coating drug-layered microcrystalline cellulose cores with cellulosic polymers to high weight gains (up to 200%). The first coating formulation consisted of a soluble polymer, hydroxypropylcellulose (HPC), which forms a hydrogel that delays release. The second formulation consisted of a 1:1 ratio of HPC and ethylcellulose. The thickness of both types of films directly correlated to the delay in release of pilocarpine HCl. The formulations for each prototype are shown below in Table 12.

TABLE 12

High weight gain cellulosic coatings

| Experiment Reference | Film Component | % w/w |
|---|---|---|
| M, N | HPC EF | 45.45 |
|  | EC N10 | 45.45 |
|  | Talc | 9.10 |
| O | HPC EF | 87 |
|  | Plasacryl | 13 |

Beads having the following weight gains were produced: 75%, 100%, 125%, 150%, 175%, and 200%. This set of beads exhibited a wide range of lag times, followed by immediate release. The delay in release is controlled by the thickness of the film. The dissolution data, obtained using the procedure of Example 2, are shown in Tables 13 and 14.

TABLE 13

Samples M and N Dissolution Data
% Dissolved at Time Point (min)

| Sample Description | 0 | 5 | 12 | 20 | 30 | 45 | 60 | 75 | Infinity |
|---|---|---|---|---|---|---|---|---|---|
| M-1 (75%) | 0 | 0 | 0 | 12 | 76 | 94 | 96 | 98 | 98 |
| M-2 (100%) | 0 | 0 | 0 | 1 | 33 | 90 | 95 | 96 | 96 |
| N-1 (125%) | 0 | 0 | 0 | 0 | 2 | 74 | 98 | 100 | 100 |
| N-2 (150%) | 0 | 0 | 1 | 0 | 0 | 27 | 89 | 98 | 99 |
| N-3 (175%) | 0 | 0 | 0 | 0 | 0 | 6 | 68 | 96 | 99 |
| N-4 (200%) | 0 | 0 | 0 | 1 | 0 | 1 | 28 | 83 | 93 |

TABLE 14

Sample O Dissolution Data
% Dissolved at Time Point (min)

| Sample Description | 0 | 5 | 12 | 20 | 30 | 45 | 60 | 75 | Infinity |
|---|---|---|---|---|---|---|---|---|---|
| O-1 (80%) | 0 | 0 | 5 | 25 | 48 | 67 | 76 | 80 | 82 |
| O-2 (100%) | 0 | 0 | 2 | 15 | 40 | 62 | 72 | 78 | 83 |
| O-3 (120%) | 0 | 0 | 0 | 3 | 23 | 53 | 70 | 79 | 86 |
| O-4 (140%) | 0 | 0 | 1 | 3 | 15 | 46 | 65 | 76 | 83 |
| O-5 (150%) | 0 | 0 | 0 | 2 | 14 | 48 | 66 | 76 | 83 |

Example 7

Cevimeline Bead Formation

Cevimeline beads are produced in substantially the same manner as pilocarpine beads, as described above, except that cevimeline is used instead of pilocarpine.

Example 8

Muscarinic Antagonist Bead Formation

Beads containing a muscarinic antagonist selected from the group consisting of the muscarinic antagonist is selected from the group consisting of 5-hydroxymethyl tolterodine, fesoterodine, oxybutynin, solifenacin, darifenacin, trospium, imidafenacin, propiverine, and dicyclomine are prepared in substantially the same manner as tolterodine beads, as described above, except that the specific muscarinic antagonist is used instead of tolterodine.

What is claimed is:

1. A pharmaceutical formulation comprising:
   a plurality of delayed-immediate release first beads and a plurality of immediate release second beads wherein:
   each first bead comprises:
     a core;
     a first layer comprising pilocarpine or a pharmaceutically acceptable salt; and
     a second layer comprising hydroxypropylcellulose and ethylcellulose,
     wherein the second layer comprises a ratio of hydroxypropylcellulose to ethylcellulose between about 5:1 to about 1:5 by weight; and
   each second bead comprises:
     a core; and
     a first layer comprising a muscarinic antagonist or a pharmaceutically acceptable salt thereof.

2. The pharmaceutical formulation of claim 1, wherein the muscarinic antagonist is oxybutynin.

3. The pharmaceutical formulation of claim 1, wherein the core of each first bead comprises a cellulose polymer, or silicon dioxide, or a sugar, selected from the group consisting of glucose, sucrose, lactose, mannitol, xylitol, and sorbitol.

4. The pharmaceutical formulation of claim 1, wherein the first layer of each first bead comprises between about 1% to about 50%, about 2% to about 40%, about 5% to about 30%, about 7% to about 25%, about 8% to about 15%, or about 12% of the total weight of the bead.

5. The pharmaceutical formulation of claim 1, wherein the pilocarpine or pharmaceutically acceptable salt thereof is present in an amount selected from the group consisting of about 0.5 mg to about 50 mg, about 3 mg, about 4 mg, about 5 mg, about 6 mg, about 10 mg, about 11 mg, and about 12 mg.

6. The pharmaceutical formulation of claim 2, wherein the oxybutynin or pharmaceutically acceptable salt thereof is present in an amount selected from the group consisting of about 0.1 mg to about 100 mg, about 3 mg, about 4 mg, about 5 mg, about 6 mg, about 7 mg, about 7.5 mg, about 8 mg, about 10 mg, and about 12 mg.

7. The pharmaceutical formulation of claim 1, wherein the first layer of each first bead further comprises a de-tackifier or a glidant selected from the group consisting of talc, glyceryl monostearate, calcium stearate, and magnesium stearate.

8. The pharmaceutical formulation of claim 1, wherein the second layer of each first bead further comprises a plasticizer selected from the group consisting of a phthalate, a trimellitate, an adipate, a sebacate, an organophosphate, a maleate, a sulfonamide, a glycols or polyether, an acetylated monoglyceride, and an alkyl citrate.

9. The pharmaceutical formulation of claim 1, wherein the first layer of each first bead further comprises a lipid excipient selected from the group consisting of glyceryl behenate, glycerol esters of fatty acids, glyceryl dibehenate, behenoyl macrogoglycerides, glyceryl distearate, glycerol distearate, glyceryl palmitostearate, lauroyl macrogoglycerides, stearoyl macrogoglycerides, abitec products, glyceryl mono-oleate, medium chain mono- & diglycerides, glyceryl monocaprylate, glyceryl tricaprylate/caprate/stearate, hydrogenated vegetable oil, hydrogenated cottonseed oil, hydrogenated soybean oil, hydrogenated soybean oil and castor wax, polyoxyethylene 8 caprylic/capric glycerides, polyoxyethylene 6 caprylic/capric glycerides, polyoxyethylene 32 lauric glycerides, polyoxyethylene 6 prop. glycol esters, polyoxyethylene 7 coconut glycerides, polyoxyethylene 30 coconut glycerides, polyoxyethylene 80 coconut glycerides, polyoxypropylene 15 stearyl ether, polyoxyethylene 26 glyceryl ether, polyoxyethylene 35 soybean glycerides, polyoxyethylene 20 sorbitol, polyoxypropylene 3 myristyl ether, polyoxypropylene 10 cetostearyl ether, palm kernelamide diethanolamide, triglycerol monooleate, sasol products, hydrogenated coco-glycerides, cetyl palmitate, trimyristin, tripalmitin, tristearin, hydrogenated palm oil, glyceryl monostearate, glyceryl stearate, cetearyl alcohol, cetyl alchohol, capric triglyceride, acetylated glycerides, glyceryl cocoate, and polyethylene glycol.

10. The pharmaceutical formulation of claim 1, wherein the core of each second bead comprises a cellulose polymer, or silicon dioxide, or a sugar, selected from the group consisting of glucose, sucrose, lactose, mannitol, xylitol, and sorbitol.

11. The pharmaceutical formulation of claim 1, wherein the core of each second bead comprises an amount selected from the group consisting of about 10% to about 90%, about 25% to about 85%, about 40% to about 80%, and about 75% of the total weight of the bead.

12. The pharmaceutical formulation of claim 1, wherein the first layer of each second bead comprises an amount selected from the group consisting of about 1% to about 50%, about 2% to about 40%, and about 4% to about 25% of the total weight of the bead.

13. The pharmaceutical formulation of claim 1, wherein each second bead further comprises:
a de-tackifier or a glidant selected from the group consisting of talc, glyceryl monostearate, calcium stearate, and magnesium stearate; and
a plasticizer selected from the group consisting of a phthalate, a trimellitate, an adipate, a sebacate, an organophosphate, a maleate, a sulfonamide, a glycols or polyether, an acetylated monoglyceride, and an alkyl citrate.

14. The pharmaceutical formulation of claim 1, wherein each second bead further comprises a second layer comprising a soluble-film forming polymer.

15. The pharmaceutical formulation of claim 14, wherein the soluble film-forming polymer is selected from the group consisting of hydroxyethylcellulose, hydroxypropylcellulose, hydroxypropylmethylcellulose, carboxymethylcellulose, maltodextrin, sucrose, modified starch, a salt of alginic acid, carageenan, polyvinylpyrrolidone (PVP) or polyvinylpolypyrrolidone (PVPP).

16. A pharmaceutical composition comprising:
a plurality of immediate release beads comprising oxybutynin or pharmaceutically acceptable salt thereof; and
a plurality of delayed-immediate release beads each comprising:
a core;
a first layer comprising pilocarpine, or a pharmaceutically acceptable salt thereof and a polymer; and
a second layer comprising hydroxypropylcellulose and ethylcellulose,
wherein the second layer comprises a ratio of hydroxypropylcellulose to ethylcellulose between about 5:1 to about 1:5 by weight.

17. The pharmaceutical composition of claim 16, wherein the core comprises a cellulose polymer, or silicon dioxide, or a sugar, selected from the group consisting of glucose, sucrose, lactose, mannitol, xylitol, and sorbitol.

18. The pharmaceutical composition of claim 16, wherein the first layer comprises an amount selected from the group consisting of about 1% to about 50%, about 2% to about 40%, about 5% to about 30%, about 7% to about 25%, about 8% to about 15%, and about 12% of the total weight of the bead.

19. The pharmaceutical composition of claim 16, wherein the second layer further comprises a soluble film-forming polymer selected from the group consisting of hydroxyethylcellulose, hydroxypropylcellulose, carboxymethylcellulose, maltodextrin, sucrose, modified starch, a salt of alginic acid, carageenan, polyvinylpyrrolidone (PVP) or polyvinylpolypyrrolidone (PVPP).

20. The pharmaceutical composition of claim 16, wherein the second layer further comprises an insoluble film-forming polymer selected from the group consisting of cellulose acetate phthalate, hydroxypropylmethylcellulose phthalate, insoluble gums, a polymethacrylate, a polyvinyl alcohol, shellac, and polyvinyl acetate phthalate.

21. The pharmaceutical composition of claim 16, wherein the first layer further comprises a de-tackifier or a glidant selected from the group consisting of talc, glyceryl monostearate, calcium stearate, and magnesium stearate.

22. The pharmaceutical composition of claim 16, wherein the second layer_further comprises a plasticizer selected from the group consisting of a phthalate, a trimellitate, an adipate, a sebacate, an organophosphate, a maleate, a sulfonamide, a glycols or polyether, an acetylated monoglyceride, and an alkyl citrate.

23. The pharmaceutical composition of claim 16, wherein the first layer further comprises a lipid excipient selected from the group consisting of glyceryl behenate, glycerol esters of fatty acids, glyceryl dibehenate, behenoyl macrogoglycerides, glyceryl distearate, glycerol distearate, glyceryl palmitostearate, lauroyl macrogoglycerides, stearoyl macrogoglycerides, abitec products, glyceryl mono-oleate, medium chain mono- & diglycerides, glyceryl monocaprylate, glyceryl tricaprylate/caprate/stearate, hydrogenated vegetable oil, hydrogenated cottonseed oil, hydrogenated soybean oil, hydrogenated soybean oil and castor wax, polyoxyethylene 8 caprylic/capric glycerides, polyoxyethylene 6 caprylic/capric glycerides, polyoxyethylene 32 lauric glycerides, polyoxyethylene 6 prop. glycol esters, polyoxyethylene 7 coconut glycerides, polyoxyethylene 30 coconut glycerides, polyoxyethylene 80 coconut glycerides, polyoxypropylene 15 stearyl ether, polyoxyethylene 26 glyceryl ether, polyoxyethylene 35 soybean glycerides, polyoxyethylene 20 sorbitol, polyoxypropylene 3 myristyl ether, polyoxypropylene 10 cetostearyl ether, palm kernelamide diethanolamide, triglycerol mono-oleate, sasol products, hydrogenated coco-glycerides, cetyl palmitate, trimyristin, tripalmitin, tristearin, hydrogenated palm oil, glyceryl monostearate, glyceryl stearate, cetearyl alcohol, cetyl alchohol, capric triglyceride, acetylated glycerides, glyceryl cocoate, and polyethylene glycol.

24. The pharmaceutical composition of claim 16, wherein the pilocarpine, or a pharmaceutically acceptable salt thereof, is present in an amount selected from the group consisting of about 0.5 mg to about 50 mg, about 3 mg, about 4 mg, about 5 mg, about 6 mg, about 10 mg, about 11 mg, and about 12 mg; and the oxybutynin, or pharmaceutically acceptable salt thereof, is present in an amount selected from the group consisting of about 0.1 mg to about 100 mg, about 3 mg, about 4 mg, about 5 mg, about 6 mg, about 7 mg, about 7.5 mg, about 8 mg, about 10 mg, and about 12 mg.

25. The pharmaceutical composition of claim 16, wherein the weight of the second layer is between about 75% to about 250% of the weight of the bead prior to application of the second layer.

26. The pharmaceutical composition of claim 16, wherein the ratio by weight of hydroxypropylcellulose and ethylcellulose is about 1:1.

27. The pharmaceutical composition of claim 16, wherein the plurality of beads release less than 20% of the initial amount of pilocarpine, or a pharmaceutically acceptable salt thereof, in the composition when immersed for 20 minutes in 0.1 N HCl, and wherein the plurality of beads release more than 90% of the initial amount of pilocarpine, or a pharmaceutically acceptable salt thereof, in the composition at a time point 30 minutes after the less than 20% of the pilocarpine has been released when immersed in 0.1 N HCl.

28. The pharmaceutical composition of claim 8, wherein the plasticizer is dibutyl sebacate.

29. The pharmaceutical composition of claim 13, wherein the plasticizer is dibutyl sebacate.

30. The pharmaceutical composition of claim 22, wherein the plasticizer is dibutyl sebacate.

* * * * *